United States Patent [19]
Sekellick et al.

[11] Patent Number: 5,641,656
[45] Date of Patent: Jun. 24, 1997

[54] NUCLEIC ACIDS ENCODING AVIAN INTERFERON (IFN) PROTEINS AND RECOMBINANT METHODS USING THEM

[75] Inventors: Margaret J. Sekellick; Philip I. Marcus, both of Storrs; Anthony F. Ferrandino, Bolton, all of Conn.

[73] Assignee: University of Connecticut, Storrs, Conn.

[21] Appl. No.: 139,909

[22] Filed: Oct. 22, 1993

[51] Int. Cl.$^6$ ............... C12N 15/20; C12N 1/21; C07K 14/465; C07K 14/555
[52] U.S. Cl. ............... 435/69.51; 435/252.3; 435/252.33; 435/254.11; 435/320.1; 536/23.52; 536/24.31; 530/351
[58] Field of Search ............... 530/351; 424/85.4, 424/85.6, 85.7; 536/23.52, 24.31; 435/69.51, 320.1, 91.1, 252.3, 252.33, 254.11, 240.2

[56] References Cited

FOREIGN PATENT DOCUMENTS

| | | |
|---|---|---|
| 0088622 | 9/1983 | European Pat. Off. |
| 89/01972 | 9/1989 | WIPO |
| 93/15185 | 8/1993 | WIPO |

OTHER PUBLICATIONS

Moehring et al. *Nature* 226: 360–361 (1970).
Pestka *Methods in Enzymology* 78: 189–192 (1982).
Pestka *Methods in Enzymology* 78: 192–195 (1982).
Rösil et al. *Eur J. Biochem* 132: 361–367 (1983).
Wilson et al. *J. Mol Biol* 166: 457–475 (1983).
Himmler et al *DNA* 5(5): 345–356 (1986).
Biladi et al. *J of Interferon Res* 13(Suppl 1) :593 (Oct. 1993).
Shuman, R.M., "Production of transgenic birds," *Experientia* 47(9) : 897–905 (1991).
Tamai, Tadakazu et al., "Cloning and expression of flatfish (*Paralichthys olivaceus*) interferon cDNA," *Biochimica et Biophysica Acta* 1174(2):182–186 (1993).
Sekellick, Margaret J. et al., "Chicken Interferon cDNA Probe," *Journal of Interferon Research* 13, Suppl. 1:S68, Abstract PW1–2 of the 1993 Annual Meeting of the ISICR, Tokyo, Japan (1993).
Krempien, Ursula et al., "Purification of Chick Interferon by Zinc Chelate Affinity Chromatography and Sodium Dodecylsulfate–Polyacrylamide Gel Electrophoresis," *Journal of Interferon Research* 5(1):209–214 (1985).
Kohase, Masayoshi et al., "Purification and Characterization of Chick Interferon Induced by Viruses," *J. Gen. Virol.* 67(1):215–218 (1986).
Digby, M. R., et al. (1995) J. Interferon and Cytokine Res. 15:939–945.
Watson, G., et al. (1984) Antiviral Res. 4, specialissue [ISIR Congr. Biol. IFN System], p. 63, abstract No. B25.
Kohase, M., et al. (1986) J. Gen. Virol. 67:215–218.
Guggenheim, M. A., et al. (1968) Science 159: 542–543.
Salter, Donald W. et al., "Transgenic Chickens: Insertion of Retroviral Genes into the Chicken Germ Line," *Virology*, 157:236–240 (1987).

Salter, Donald W. et al., "Lack of genetic transmission of avian leukosis proviral DNA in viremic Japanese quail," (Abstract) Proceedings of the Second Symposium on Genetic Engineering of Animals, Cornell University, Ithaca, NY (1989). *Journal of Reproduction and Fertility*, Supplement 41 (1990).
Fernando, Lawrence P. and Andrews Glen K., "Cloning and expression of an avian metallothionein–encoding gene," *Gene*, 81:177–183 (1989).
Marcus, Philip I. and Sekellick, Margaret J., "Interferon Induction by Viruses. XVI. 2–Aminopurine Blocks Selectively and Reversibly an Early Stage in Interferon Induction," *J. Gen. Virol.*, 69:1637–1645 (1988).
Svitlik, Charles and Marcus, Philip I., "Interferon Induction by Viruses. XII. Inhibition of Protein Synthesis Renders Aged Chick Embryo Cells Refractory to Interferon Induction," *J. Gen. Virol.*, 66:883–886 (1985).
Sekellick, Margaret J. and Marcus, Philip I., "Interferon Induction by Viruses. XIV. Development of Interferon Inducibility and Its Inhibition in Chick Embryo Cells Aged" *In Vitro, Journal of Interferon Research*, 5:651–667 (1985).
Sekellick, Margaret J. and Marcus, Philip I., "Induction of High Titer Chicken Interferon," *Methods in Enzymology*, 119:115–125 (1986).
Yoshida, Itsuroand Marcus, Philip I., "Interferon Induction by Viruses. XX. Acid–Labile Interferon Accounts for the Antiviral Effect Induced by Poly(rI).Poly(rC) in Primary Chick Embryo Cells," *Journal of Interferon Research*, 10:461–468 (1990). 2
Marcus, Philip I. et al., "Interferon Induction by Viruses. XXI. Vesicular Stomatitis Virus: Interferon Inducibility as a Phylogenetic Marker," *Journal of Interferon Research*, 12:297–305 (1992).
Sekellick, Margaret J. et al., "Development of the Interferon System. I. In Chicken Cells Development in Ovo Continues on Time In Vitro," *In Vitro Cell. Dev. Biol.*, 26:997–1003 (1990).
Hough, S. and R.H. Foote, "The Effect of the Cornell Particle Gun on Bull and Rabbit Spermatozoa," Abstract, *Biology of Reproduction*, 42:65 (1990).
Crittenden, L.B. and Salter, D.W., "Expression and mobility of retroviral inserts in the chicken germ line," *Transgenic Models in Medicine and Agriculture*, pp. 73–87, Wiley–Liss, Inc. (1990).
Reed, M.L. et al., "Microinjection of liposome–encapsulated DNA into murine and bovine blastocysts," Abstract, *Theriogenology*, 29(1):293 (1988).

(List continued on next page.)

*Primary Examiner*—David L. Fitzgerald
*Attorney, Agent, or Firm*—Hamilton, Brook, Smith & Reynolds, P.C.

[57] ABSTRACT

A chicken interferon gene coding for the amino acid sequence of SEQ ID NO: 2 is disclosed. There is also disclosed a method of producing chicken interferon recombinantly, a method of isolating other non–mammalian interferon genes and a method of making a transgenic fowl having the chicken interferon gene incorporated therein.

15 Claims, No Drawings

OTHER PUBLICATIONS

Coonrod, S.A. et al., "Successful non-surgical collection of ovine embryos," Abstract, *Theriogenology*, 25(1):149 (1986).

Shuman, R.M. et al., "Tissue specificity of a retrovirus gene transfer vector revealed by expression of a bacterial marker gene," Abstracts of the 9th Annual Meeting of the Southern Poultry Science Society, *Poultry Science*, 67, Supplement 1:156 (1988).

Shuman, R.M., "Use of retrovirus vectors for gene insertion in poultry and swine," *J. of Dairy Sci.*, 72(suppl. 1):61 (1989).

Sekellick, Margaret J. et al., "Chicken Interferon Gene: Cloning, Expression, and Analysis," *Journal of Interferon Research*, 14:83–91 (1994).

NUCLEIC ACIDS ENCODING AVIAN INTERFERON (IFN) PROTEINS AND RECOMBINANT METHODS USING THEM

GOVERNMENT SUPPORT

The invention described herein was supported in whole or in part by Grant Number AI18381 from the National Institute of Allergy and Infectious Disease. The Government has certain rights in the invention.

BACKGROUND OF THE INVENTION

Chicken interferon (IFN) is a valuable protein useful in protecting and treating chickens and other fowl from avian viral diseases. Induction of interferon by virus has been successful in primary chick embryo cells "aged" in vitro, with yields ranging from 300 to more than 8,000 units of interferon per $10^7$ cells (Marcus, Sekellick and Nichol, *Journal of Interferon Research* 12:297–305 (1992)).

In addition it is possible that some important parasitic diseases of chickens like that caused by Eimeria may be controllable by interferon through its effects on the immune system. Interferon is gaining increased attention as an antiparasitic agent, (Murray, *Journal Interferon Research*, 12:319–322 (1992)).

Many factors determine how much interferon is induced by a particular virus. These factors include its origin and passage history, the host cell, incubation conditions and time, and the multiplicity of infection. Stewart, "The Interferon System", 2nd. ed., Vienna:Springer-Verlag, pp 27–57; Marcus, Sekellick and Nichol, *Journal of Interferon Research*, 12:297–305 (1992).

SUMMARY OF THE INVENTION

This invention relates to isolated genes and recombinant DNA coding for non-mammalian interferon, processes for preparing and isolating them and methods of use therefor. The isolated gene preferably codes for avian, fish or reptile interferon. Preferred embodiments of avian interferon include fowl, such as chickens, turkeys, ducks, and exotic birds, such as parrots, cockatoos, cockatiels, and other commercially valuable birds. The nucleotide sequence encoding chicken interferon is described herein.

This invention also relates to a method of producing recombinant chicken interferon which comprises culturing a transformed microorganism capable of producing chicken interferon, said microorganism having inserted therein a recombinant chicken interferon gene such as the DNA sequence of SEQ ID NO: 1, and recovering said chicken interferon. The amino acid sequence encoding the signal and mature IFN protein has been deduced and is described herein (SEQ ID NO: 2). The transformed microorganism employed may be any host cell or cells capable of producing the recombinant protein. Preferably the host cell is derived from a prokaryote, eukaryote or mammalian cell culture, with prokaryote being most preferred, eg. *E. coli*.

A cDNA probe is also described herein and comprises the nucleotide sequence of SEQ ID NO: 3. The cDNA probe can be used to isolate and identify other non-mammalian interferon genes, such as other avian species, fish and reptiles, due to ancestral homology. A useful probe will comprise at least about a twenty base pair segment of the DNA sequence of SEQ ID NO: 1 which will bind to the complement of said sequence.

The invention also pertains to a plasmid comprising a) DNA sequence coding for non-mammalian interferon, preferably avian, fish and reptile interferon, most preferably chicken interferon, and b) a promoter sequence operably linked to said DNA sequence, preferably chicken metallothionein.

The novel plasmid constructs of this invention can be used to produce abundant quantities of recombinant interferon for administration to fowls and exotic birds, in order to prevent viral and/or parasitic infections. Alternatively, the DNA and constructs containing the DNA of this invention can be used to produce transgenic fowl. The transgenic fowl would harbor an inducible plasmid for the transient expression of chicken interferon. Such transient expression would be induced at a time in the development of the fowl which would not retard growth but would provide protection against viral and/or parasitic infections.

This invention further pertains to transgenic fowl wherein its germ cells and/or somatic cells contain the recombinant DNA comprising an isolated avian interferon DNA introduced at an embryonic stage, and a method of making the same. Preferably, the recombinant DNA is substantially endogenous to the transgenic fowl, such as that coding for chicken interferon where the transgenic fowl is a transgenic chicken. In one embodiment, a promoter sequence heterologous to the chicken promoter can be operably linked to the recombinant DNA coding for chicken interferon in order to selectively induce expression of the interferon gene. An example of a heterologous promoter is the chicken metallothionein promoter which can be regulated by providing a source of metallic ions to the fowl. By this method, it is possible to treat or prevent viral and/or parasitic infection by inducing transcription of the DNA in the transgenic fowl.

DETAILED DESCRIPTION OF THE INVENTION

The first DNA nucleotide sequence and probe therefor that codes for a non-mammalian interferon, namely chicken interferon, are described herein. The nucleotide sequence coding the complete chicken interferon gene has been determined and is set forth in SEQ ID NO: 1. The sequence is 763 nucleotides in length and contains the following nucleotides starting at the 5' end:

54 bases of the 5' flanking sequence, 93 bases coding a 31 amino acid signal protein, 486 bases coding the mature chicken interferon protein, 3 bases for a stop signal, 127 bases comprising the 3' flanking region and a poly(A) tail.

The probe is the first DNA nucleotide sequence found to be specific for the chicken interferon messenger RNA (mRNA). A special system of "aged" primary chick embryo cells (Sekellick and Marcus, *Methods in Enzymology*, 119:115–125 (1985)), was used to induce the messenger RNA for chicken interferon. This chicken interferon probe shares less than 50% homology with reported mammalian interferon α and β species.

Primers were also designed to capture and synthesize a portion of the chicken interferon gene. PCR products were then produced, using these primers to amplify sequences from messenger RNA obtained from "aged" primary chick embryo cells, according to Sekellick and Marcus, "Methods in Enzymology", 19:115–125, (1985). A successful Northern blot using the chicken interferon DNA probe demonstrating the size of the interferon messenger RNA was obtained. The chicken interferon DNA probe is a 269 base sequence that includes two primer regions. The Northern blot was obtained using the chicken interferon DNA probe demonstrating an inducible messenger RNA with proper size and characteristics in response to control treatments such as cycloheximide, actinomycin D, indomethacin and 2-aminopurine in UV-avian reovirus infected "aged" primary chick embryo cells, as well as poly I-poly C treatment, and infection with vesicular stomatitis virus (VSV) serotype Indiana (IN) #22-20 and infection with VSV (IN) #22-25 in the same system.

The cDNA probe obtained by this method has the nucleotide sequence of SEQ ID No: 3. The probe comprises a 269 nucleotide sequence having a 5' primer region of 32 bases, a 3' primer region of 20 bases and a 217 base partial sequence of the chicken interferon gene. The probe can be manufactured by alternative processes well known in the art. Other useful probes, as discussed above, can be made in the same or similar manner. Preferred probes include those comprising at least about a 20 base pair segment of the DNA sequence of SEQ ID NO: 1 which will bind to the complement of the interferon gene. Preferably the base pair segment will be located in the region which corresponds to about nucleotide 145 to about nucleotide 195 of SEQ ID NO: 1. A highly conserved region is found at the 165–175 segment.

The probe can then be used in screening a chicken cDNA library, according to the methods described in detail below. In this procedure, 5 clones containing full-length coding regions and 1 truncated clone were isolated. The mRNA coding for chicken interferon can thereby successfully be obtained. Synthesis of cDNA from mRNA coding for chicken interferon can be performed by methods described in detail below.

The thus obtained cDNA can be incorporated into a cloning vehicle to obtain transformants. Cloning vehicles which can be used in this invention include plasmids, such as the SuperScript Plasmid System for cDNA Synthesis and Plasmid Cloning (available from GIBCO/BRL; Life Technologies, Inc.). The cDNA thus cloned is produced with Not I and Sal I termini for directional cloning into the Not I- Sal-I-Cut plasmid pSPORT I.

Using these plasmids, or cloning vehicles, the DNA can be incorporated into an appropriate cell, such as a prokaryote or eukaryote, according to methods known in the art, such as *Current Protocols in Molecular Biology*, F. Ausubel, et al., (Eds.). The transformants are cultured to thereby express the cell protein. Confirmation of the expression of chicken interferon can be achieved by known assays. The expressed chicken interferon can be isolated from the culture according to known techniques, including, for example, *Current Protocols in Molecular Biology*.

The amino acid sequence encoding the signal region and mature chicken interferon protein has been deduced (SEQ ID NO: 1). The mature protein has the amino acid sequence of SEQ ID NO: 2. Chicken interferon is a 20–30 KD glycosylated protein which is acid stable. The nonglycosylated molecule is an 18 KD protein. Directed mutation at the 4 potential N-glycosylation sites could lead to chicken interferon molecules with varying degrees of stability and enhanced biological activity. The 6 cysteine residues in the chicken interferon molecule provide the possibility of altering the number of potential disulfide bonds and, hence, stability properties of the molecule, as has been reported for mammalian interferons. (Day et al., *Journal of Interferon Research*, 12:139–143 (1992)). In this context, the acid labile form of chicken interferon reported by Yoshida and Marcus (*Journal of Interferon Research*, 19:461–468 (1990)), may reflect such transient changes.

In mammals, four families of type I interferon genes have been described, (e.g. interferon-alpha, beta, -omega and -tau) and one family of type II interferon (e.g. interferon-gamma). Southern analysis of genomic chicken DNA that have been carried out using probes described herein for chicken interferon indicates there may be only one chicken interferon gene. At the amino acid level, the chicken interferon gene shares only about 22% homology with all other type I mammalian interferons, i.e., interferons -alpha, -beta, -omega and -tau, and less than 3% homology with the type II mammalian interferon, i.e., interferon -gamma. It has been determined herein that chicken interferon is unusual in its content of 6 cysteine residues and 4 potential N-glycosylation sites. Because of its ancestral origin, the chicken interferon gene can be useful in detecting and isolating interferon genes of other nonmammalian species, for example, fish and reptiles.

Mammalian interferons have been engineered genetically to display more desirable traits, for example, altered host range and enhanced specific activity. Day et al., Ibid. Thus, using similar techniques it may be possible that the chicken interferon gene could be manipulated similarly.

Recombinant chicken interferon can then be administered to fowl, preferably chickens and exotic birds, in an amount effective to treat or prevent viral and/or parasitic infections. Examples of avian viruses for which chicken interferon could be used to treat/prevent diseases caused thereby include but are not limited to orthomyxovirus (eg., influenza); paramyxovirus (eg., Newcastle disease virus); coronavirus (eg., infectious bronchitis); hepadnavirus (eg., hepatitis); poxvirus (eg., fowl pox); adenovirus (eg., adenovirus); retrovirus (eg., leukosis virus); herpesvirus (eg., Marek's disease). Parasitic infection such as that caused by Eimeria or other parasite which is controllable by interferon can also be treated/prevented using the recombinant interferon of this invention.

The interferon can be formulated into a veterinary preparation, for example, in semisolid or liquid form, which contains the recombinant chicken interferon, as an active ingredient, in admixture with suitable organic or inorganic carriers or excipients. The active ingredient may be compounded, for example, with the usual non-toxic, veterinary carriers for solutions, emulsions, suspensions and any other form suitable for use. The carriers which can be used include albumin, water, glucose, lactose, gum acacia, gelatin, mannitol, starch paste, saline, and other carriers suitable for use in manufacturing preparations. In addition auxiliary, stabilizing and thickening agents may be used.

The composition is administered to the fowl by an effective delivery method. The preferred mode of administration is parenteral. The dosage of effective amount of chicken interferon will depend upon the age and condition of the fowl. A daily dose typically is $2-10 \times 10^4$ units/kg, preferably $5 \times 10^4$ units/kg. See Sekellick and Marcus (1985), Ibid. for standard techniques for determining the unit measure for interferon.

An alternative method for preventing and/or treating viral and parasitic infection is to produce transgenic fowl where the fowl harbors an inducible gene encoding interferon endogenous to that fowl. The method of making the transgenic fowl includes the steps of introducing and incorporating recombinant DNA comprising a nucleotide sequence coding for avian interferon at an embryonic stage, preferably in the sperm, ovum, zygote or embryo, of a fowl and incubating said embryonic stage under conditions necessary for development of the fowl. Preferably, the fowl is a chicken. For example, the transgenic fowl can be prepared by incorporating the cDNA, preferably with a predetermined promoter, into a eukaryotic expression vector, for example, plasmid pSV3-neo (ATCC accession number 37150). The thus obtained plasmid DNA can then be incorporated into the desired fowl by methods generally recognized in the art. Expression of the interferon in the fowl can protect the fowl from viral and/or parasitic disease.

The chicken interferon gene, generally, is operably placed behind promoters that will respond to stimuli other than the endogenous promoter for the gene. Double stranded (DS) RNA can be used to stimulate the promoter (Marcus, "In Interferon 5" Edition I, Gresser, Academic Press, pp. 115–180, 1983). A chicken metallothionein promoter can also be used (Fernando and Andrews, Gene, 81:177–183 (1989)), so that the cells or chickens containing this construct would respond to metal ions such as $Cd^{++}$ or $Zn^{++}$ and produce interferon transiently, as desired.

The metal ions can be administered by any effective means, including orally or parenterally. The most preferred embodiment is oral administration. The metallic ions can be formulated in any effective composition. Suitable carriers include those described above. For example, the metallic ions can be incorporated into the fowl's feed, where ingestion of the metallic ion induces the metallothionein promoter. The effective dosage of the metallic ions can be readily determined by the skilled artisan, and depend upon the age and condition of the fowl.

The invention will be used to establish transgenic chickens that either constitutively express the chicken interferon gene, so that the chicken displays resistance to a broad spectrum of viral infections comparable to that observed in vitro, or transiently express chicken interferon as required to prevent or combat virus infection. Transiently expressed interferon is preferred because constitutive expression results in levels of interferon that might be deleterious to embryonic development. See Müller et al., Gene, 121:263–270 (1992) in which the early expression of the Mx'1 gene was shown to be deleterious in transgenic pigs. In activating the interferon gene system, this approach has the advantage of bringing the interferon system in to play only when required, as during outbreak of a viral disease, and not during critical developmental stages in the establishment of the transgenic chickens.

Chicken interferon expressed in this manner has the added advantage of also activating the Mx system, as it does naturally, and render the chickens resistant to avian influenza virus as well. Avian influenza and other avian viruses can decimate flocks, and chickens that were intrinsically resistant to virus or could be activated to resistance by simply manipulating the feed would be of great commercial value. The chicken industry is a multibillion dollar industry.

Any effective method for incorporating the cDNA plasmid into the fowl can be used. Examples of such methods include microinjection, electroporation, sperm transfection, liposome fusion, and microprojectile bombardment. The desired gene can also be introduced into sperm cells by the Cornell particle gun. Microprojectile bombardment employing the Cornell particle gun was developed to deliver desired genetic constructs into cells by firing DNA-coated inert microparticles, such as tungsten into the cells. Hough and Foote, "The Effect of the Cornell Particle Gun on Bull and Rabbit Spermatatozoa", Abs. Biol. Reprod. Suppl. 1 42:65, (1990); U.S. Pat. No. 5,100,792, Sanford et al., issued Mar. 31, 1992, incorporated by reference.

Another method for producing transgenic chickens is using "one round" retroviral vectors. See Salter, et al., Transgenic Chickens: Insertion of Retroviral Genes into the Chicken Germ Line, Virology, 157:236–240 (1987), for example. It is reported that insertion of foreign DNA in early chicken embryos occurred where the DNA was injected into the yolk near the embryo in a newly laid fertile egg. The procedure employed is described in Salter et al., Poult. Sci., 65:1445–1458 (1986), which is incorporated herein by reference.

It is particularly advantageous to modify the retroviral vector to improve their efficiency and reduce pathogenicity. One method which may be employed is the deletion of at least one replication gene of the retroviral vector. Crittenden and Salter, Poc. UCLA Symp., Transgenic Models in Med and Agr., pp 73–87, 1990; Salter and Crittenden, Theor. Appl. Genetics, 77:457–461 (1989); Crittenden, Salter and Federspiel, Theor. Appl. Genetics, 77:505–515, 1989; Salter and Crittenden, "Proc. Discoveries in Antisense Nucleic Acids", pp 95–110, (1989); Salter et al., Virology, 157:236–240, 1987; Crittenden et al., J. Virol., 61:772–775, 1987; Crittenden, Poultry Sci., 65:1468–1473 (1986); Crittenden, Avian Dis., 30:43–46 (1986); Hughes, Poultry Sci., 65:1459:1467 (1986); Salter et al., Poultry Sci., 65:1445–1458 (1986); Crittenden and Salter, Canadian J. of Animal Science, 65:553–562 (1985).

Production of a successful transgenic chicken with non-replicating vectors has been described. Shuman, J. of Dairy Sci., 72(suppl 1):61, (1989); Lee, M. R., Ph.D. Thesis, North Carolina State University, (1989); Shuman et al., Poultry Sci., 67:136, (1988). None of these transgenic chickens contain the chicken interferon cDNA described herein.

In the method of this invention the DNA construct, discussed above, optionally with a suitable promoter, is impregnated in or coated on an inert microparticle. The DNA coated or impregnated microparticle is then delivered into the appropriate cell, including the sperm, ovum, zygote or embryo. Because sperm cells are natural vectors, it is preferred that the DNA coated microparticle is delivered into the sperm. It is preferred that the Cornell particle gun be employed in the delivery of the microparticle to the cell. However, any mode of effective delivery can be employed, including those described in the Sanford patent. While some loss of sperm motility may be experienced, application of a vacuum and addition of ATP may recapture some or all motility. Preferred ATP concentrations are 0.05–1.0 mM ATP.

Newly hatched chicks can be screened for the cDNA by routine procedures, such as by a simple dot-blot procedure, discussed in the above incorporated article.

The cDNA probe and/or the chicken interferon gene and/or any effective fragment thereof can be used as a probe to isolate the interferon gene of other avian species, fish or reptile. The method to be employed is substantially the same used and described above for isolating the chicken interferon gene.

The interferon gene so isolated can then be used, in the manner described above, for the preparation of the recombinant interferon protein or for the preparation of a transgenic animal. The recombinant interferon protein can be administered to an appropriate avian, fish or reptile in the manner described above. The administration of interferon to fish can also be accomplished, for example, by adding the interferon to the aqueous environment. The interferon may be absorbed through the gills of the fish.

Interferon can be injected into eggs to provide protection to the embryo using known techniques.

The invention will be further illustrated by the following exemplification:

EXEMPLIFICATION

MATERIALS AND METHODS

Cells and Media: Monolayers of primary chick embryo cells were prepared from 10-day-old chick embryos as previously described (Sekellick and Marcus, *Methods Enzymol.*, 119:115–125, (1986); Sekellick, Biggers and Marcus, *In Vitro Cell Dev. Biol.*, 26:997–1003 (1990)). Cells were aged in vitro without a medium change for the periods of time indicated, usually 8–10 days, to enhance their IFN-inducing capacity (Sekellick and Marcus, (1986); Sekellick, Biggers and Marcus, (1990).

Source of Viruses, Preparation and Assay: The origin, growth and source of avian reovirus as well as various strains of wild-type VSV IN have been described (Winship and Marcus, *J. Interferon Res.*, 1:155–167 (1980); Sekellick and Marcus, *J. Gen. Virol.*, 70:405–415 (1989); Sekellick and Marcus, *Virology*, 95:36–47 (1979); Marcus, Sekellick & Nichol (1992); Marcus et al., *J. Interferon Res.*, 13:547 (1993)). Plaque assays, stock amplification and UV radiation of avian reovirus were performed as previously described using primary chick embryo cells as host (Winship and Marcus, (1980)). VSV preparations were grown and plaqued in GMK-Vero cells as described previously (Sekellick and Marcus, (1989)).

IFN Induction and Assay: Details for the procedures used to induce and assay acid stable IFN in aged primary chick embryo cells have been described (Sekellick and Marcus (1986); Sekellick, Biggers and Marcus, (1990); Yoshida and Marcus, *J. Interferon Research*, 10:461–468, (1990)). UV-irradiated avian reovirus was used to infect primary chick embryo cells at a multiplicity of infection of 5 as described previously (Winship and Marcus, (1980)) in order to induce IFN maximally.

RNA Purification: Total cellular RNA was obtained from UV-irradiated-avian reovirus infected primary chick embryo cells at various times post infection. Cells were lysed with SDS/EDTA and total RNA extracted with water-saturated acid phenol followed by ethanol precipitation (Maniatis, Fritsch & Sambrook, *Molecular Cloning: A Laboratory Manual* (2nd Ed.), Cold Spring Harbor Laboratory Press (1989)). RNA extracted in this manner served as template in a PCR reaction or for Northern blot analysis.

Oligonucleotide Synthesis: Known IFN and amino acid sequences were obtained from Genbank and were aligned to minimize gaps and maximize homology. Regions exhibiting high homology near the carboxyl end and middle of the protein were examined in detail at the amino acid level, and two probes were constructed based on sequences from these regions. Nucleotide sequences were derived from amino acid sequences, favoring codon preferences observed for vertebrate species (other than mammalian), while substituting two or more nucleotides at degenerate positions. For PCR, the "downstream" primer was antisense for cDNA synthesis and the "upstream" primer was sense for amplification of the cDNA with the "downstream primer". Sense and anti-sense degenerate PCR primers corresponded to nucleotide positions 220–251 and 469–488, respectively, relative to the mouse IFN-beta gene sequence. The sense primer was a 32-mer consisting of the sequence 5'-TTGGCCATCTATGAGATGCTCCAGMANATHTT-3' (SEQ ID NO: 4). The anti-sense primer was a 20-mer consisting of the sequence 5'-CGGACCACTGTCCANGCRCA-3' (SEQ ID NO: 5).

Polymerase Chain Reaction (PCR): RNA PCR was performed according to the protocol provided with the Perkin Elmer-Cetus Geneamp RNA PCR kit. Briefly, one microgram of total RNA isolated from primary chick embryo cells that were induced to produce interferon was used in a 20 µl reverse transcription reaction using the downstream primer for cDNA synthesis. The reaction was carried out at 42° C. for 15 minutes and then at 99° C. for 5 minutes to inactivate the reverse transcriptase. After cooling to 5° C., reaction components were added to give a 100 µl volume with both primers now present at a concentration of 0.5 µM. PCR was carried out for 36 cycles of 95° C. for 1 minute, 37° C. for 1 minute and 72° C. for 1 minute.

Purification of PCR Products: PCR products were ethanol precipitated, redissolved in water, and run out on a 3% Nusieve GTG agarose (FMC) gel. The band of the expected size was cut from the gel, melted, and diluted 1:10 with sterile water. A 10 µl volume of this solution was used in another PCR reaction to amplify even more of the fragment so a sufficient amount was available for cloning. Reaction conditions were performed as before except the annealing was performed at 50° C. PCR products were again gel purified except the excised bands were purified from the agarose by spinning in a microfuge through Costar spin-X centrifuge filter units at 4° C. The samples were then extracted with sec-butanol to remove ethidium bromide, quantitated, ethanol precipitated and redissolved in sterile water.

Synthesis of the cDNA Fragment: The phagemid pBluescript KS(–) was cut out with Eco RV to produce a blunt end and also cut out with Eag I to produce a 3' overhang on the other end. The purified PCR product contained a single restriction site for Eae I toward the 5' end of the upstream primer which produced a 3' end overhang complementary to that produced by Eag I. The fragment was ligated into pBluescript under conditions favoring blunt end ligations with a molar ratio of insert:vector of 10:1. Recombinant plasmids were transformed into XL1-Blue *E. Coli*. Positive colonies were identified using blue/white colony selection. Recombinants were then verified by restriction digests that produced inserts of the expected size. A clone containing a 269-base insert (designated pCh269) was selected for use in subsequent studies.

DNA Sequencing of the Cloned PCR Fragment: Double-stranded DNA sequencing was performed using TAQuenoe Version 2.0 from USB. Plasmid was prepared from 500 ml cultures by the alkaline lysis method. Contaminating RNA was removed by lithium chloride precipitation and RNase treatment followed by organic extraction and ethanol precipitation. Plasmid was heat-denatured and flash frozen in dry ice and ethanol prior to performing sequencing reactions. Completed reactions were than analyzed on a 7% Long Ranger (J. T. Baker) polyacrylamide gel using sequencing reactions from both strands of the plasmid insert.

cDNA Cloning: Using aged primary chick embryo cells infected with UV-AVR, conditions known to produce high yields of interferon, total RNA was isolated from cells at about 8 hours post infection as described above. Poly(A)+ RNA was isolated from oligo(dT)-cellulose spun columns supplied with a Pharmacia mRNA Purification Kit. cDNA was synthesized from this poly(A)+ RNA and cloned into Not I-Sal I-cut plasmid pSPORT I using a BRL Superscript Plasmid System. Plasmid was electroporated into BRL ElectroMAX DH10B cells using the "Electroporator" electroporating apparatus from Invitrogen. Clones were screened using biotinylated-PCR product prepared from pCh269 template and hybridized to DNA from colony lifts which were UV-crosslinked to MSI nylon membranes (50 cm diameter) and detected with the Colony Images Non-Isotopic Colony/Plaque Screening Kit (USB).

DNA Sequencing of cDNA Clones: Plasmids were isolated using a standard alkaline lysis method followed by ammonium acetate precipitation (for 10 ml cultures) or lithium chloride precipitation (for 500 ml cultures). This was followed by RNase treatment to remove residual contaminating bacterial RNA. The plasmids were then sequenced using the Pharmacia AutoRead Sequencing Kit for double-stranded templates with T7 and SP6 fluorescein labelled primers (supplied by the Biotechnology Center, Univ. of CT). Following termination, sequencing reactions were analyzed on the Pharmacia Automated Laser Florescent A.L.F. DNA sequencer using a 6% polyacrylamide gel.

Northern Blot Analysis: RNA samples were run out for 3 hours on a 1% agarose gel containing 2.2M formaldehyde and transferred to a nylon membrane by capillary elution in 10X SSC. RNA was cross-linked to the dry membrane with 254 nm UV for 17 minutes. The Gibco BRL Photogene protocol was followed for probe hybridization and nonradioactive nucleic acid detection. Hybridization solutions contained 50% formamide and reactions were performed at 42° C. Stringency washes were performed under moderate conditions using 0.1% SSC and 1% (w/v) SDS at 50° C. for 30 minutes. Membranes were exposed to Kodak XAR-5 film usually for 2–4 hours to obtain a signal of sufficient intensity.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

We claim:

1. An isolated nucleic acid molecule comprising a sequence selected from the group consisting of:
   (a) the sequence of a DNA molecule isolated from an avian DNA library, wherein said DNA molecule encodes an avian type I interferon proprotein and wherein said DNA molecule hybridizes under conditions of moderate stringency to a probe having the sequence of the full-length complement of the coding sequence shown in SEQ ID NO: 1; and
   (b) a DNA molecule encoding the mature avian type I interferon which results from removal of the signal peptide of the interferon proprotein encoded by the DNA molecule of (a).

2. An isolated and purified nucleic acid molecule comprising a sequence selected from the group consisting of:
   (a) the sequence of a DNA molecule isolated from an avian DNA library, wherein said DNA molecule encodes an avian type I interferon proprotein and wherein said DNA molecule hybridizes under conditions of moderate stringency to a probe having the sequence of the full-length complement of the coding sequence shown in SEQ ID NO: 1;
   (b) a DNA molecule encoding the mature avian type I interferon which results from removal of the signal peptide of the interferon proprotein encoded by the DNA molecule of (a); and
   (c) a nucleic acid molecule which is degenerate with the DNA of (a) or (b).

3. An isolated and purified nucleic acid fragment of a molecule according to claim 2, comprising a sequence selected from the group consisting of
   at least about 20 contiguous nucleotides from the coding sequence of said isolated nucleic acid molecule, and
   at least about 20 contiguous nucleotides from the sequence of said DNA molecule isolated from an avian DNA library;
   or the complement thereof.

4. A plasmid comprising:
   a) the sequence of a nucleic acid molecule according to claim 2; and
   b) a promoter sequence operably linked to said nucleic acid sequence.

5. A plasmid according to claim 4 wherein said nucleic acid sequence is the DNA sequence shown in SEQ ID NO: 1.

6. A plasmid according to claim 5 wherein said promoter is a chicken metallothionein promoter.

7. A method of producing an avian interferon protein which comprises:
   a) culturing a microorganism transformed with a nucleic acid molecule according to either one of claims 2 or 1 under conditions suitable for the expression of said nucleic acid; and
   b) recovering said avian interferon protein from the cell culture.

8. A method according to claim 7 wherein said nucleic acid molecule encodes the amino acid sequence shown in SEQ ID NO: 2.

9. A method according to claim 8 wherein said nucleic acid molecule has the nucleotide sequence shown in SEQ ID NO: 1.

10. A method of claim 7 wherein said microorganism is a prokaryote.

11. A method of claim 7 wherein said microorganism is *Escherichia coli*.

12. An isolated and purified nucleic acid molecule coding for a chicken interferon polypeptide comprising the amino acid sequence of the mature chicken interferon shown in SEQ ID NO: 2.

13. A nucleic acid molecule according to claim 12 comprising the coding region shown in SEQ ID NO: 1.

14. A chicken interferon cDNA probe having the nucleotide sequence of SEQ ID NO: 3.

15. An isolated and purified nucleic acid molecule of at least about 20 nucleotides which hybridizes under conditions of moderate stringency to a probe having the sequence of the full-length complement of the coding sequence shown in SEQ ID NO: 1.

\* \* \* \* \*

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 767 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 55..633

( x i ) SEQUENCE DESCRIPTION: SEQ ID NO:1:

```
CGCACCACCA  CCGAGCCCCA  CCAGGCTCCT  GCCCAGCACA  ACGCGAGTCC  CACC ATG           57
                                                                Met
                                                                 1

GCT  GTG  CCT  GCA  AGC  CCA  CAG  CAC  CCA  CGG  GGG  TAC  GGC  ATC  CTG  CTG    105
Ala  Val  Pro  Ala  Ser  Pro  Gln  His  Pro  Arg  Gly  Tyr  Gly  Ile  Leu  Leu
               5                        10                       15

CTC  ACG  CTC  CTT  CTG  AAA  GCT  CTC  GCC  ACC  ACC  GCC  TCC  GCC  TGC  AAC    153
Leu  Thr  Leu  Leu  Leu  Lys  Ala  Leu  Ala  Thr  Thr  Ala  Ser  Ala  Cys  Asn
               20                       25                       30

CAC  CTT  CGC  CCC  CAG  GAT  GCC  ACC  TTC  TCT  CAC  GAC  AGC  CTC  CAG  CTC    201
His  Leu  Arg  Pro  Gln  Asp  Ala  Thr  Phe  Ser  His  Asp  Ser  Leu  Gln  Leu
          35                       40                       45

CTC  CGG  GAC  ATG  GCT  CCC  ACA  CTA  CCC  CAG  CTG  TGC  CCA  CAG  CAC  AAC    249
Leu  Arg  Asp  Met  Ala  Pro  Thr  Leu  Pro  Gln  Leu  Cys  Pro  Gln  His  Asn
50                       55                       60                       65

GCG  TCT  TGC  TCC  TTC  AAC  GAC  ACC  ATC  CTG  GAC  ACC  AGC  AAC  ACC  CGG    297
Ala  Ser  Cys  Ser  Phe  Asn  Asp  Thr  Ile  Leu  Asp  Thr  Ser  Asn  Thr  Arg
               70                       75                       80

CAA  GCC  GAC  AAA  ACC  ACC  CAC  GAC  ATC  CTT  CAG  CAC  CTC  TTC  AAA  ATC    345
Gln  Ala  Asp  Lys  Thr  Thr  His  Asp  Ile  Leu  Gln  His  Leu  Phe  Lys  Ile
               85                       90                       95

CTC  AGC  AGC  CCC  AGC  ACT  CCA  GCC  CAC  TGG  AAC  GAC  AGC  CAA  CGC  CAA    393
Leu  Ser  Ser  Pro  Ser  Thr  Pro  Ala  His  Trp  Asn  Asp  Ser  Gln  Arg  Gln
               100                      105                      110

AGC  CTC  CTC  AAC  CGG  ATC  CAC  CGC  TAC  ACC  CAG  CAC  CTC  GAG  CAA  TGC    441
Ser  Leu  Leu  Asn  Arg  Ile  His  Arg  Tyr  Thr  Gln  His  Leu  Glu  Gln  Cys
          115                      120                      125

TTG  GAC  AGC  AGC  GAC  ACG  CGC  TCC  CGG  ACG  CGA  TGG  CCT  CGC  AAC  CTT    489
Leu  Asp  Ser  Ser  Asp  Thr  Arg  Ser  Arg  Thr  Arg  Trp  Pro  Arg  Asn  Leu
130                      135                      140                      145
```

| | | | | | | | | | | | | | | | | |
|---|---|---|---|---|---|---|---|---|---|---|---|---|---|---|---|---|
| CAC | CTC | ACC | ATC | AAA | AAA | CAC | TTC | AGC | TGC | CTC | CAC | ACC | TTC | CTC | CAA | 537 |
| His | Leu | Thr | Ile | Lys | Lys | His | Phe | Ser | Cys | Leu | His | Thr | Phe | Leu | Gln | |
| | | | 150 | | | | | 155 | | | | | | 160 | | |
| GAC | AAC | GAT | TAC | AGC | GCC | TGC | GCC | TGG | GAA | CAC | GTC | CGC | CTG | CAA | GCT | 585 |
| Asp | Asn | Asp | Tyr | Ser | Ala | Cys | Ala | Trp | Glu | His | Val | Arg | Leu | Gln | Ala | |
| | | | 165 | | | | 170 | | | | | | 175 | | | |
| CGT | GCC | TGG | TTC | CTG | CAC | ATC | CAC | AAC | CTC | ACA | GGC | AAC | ACG | CGC | ACT | 633 |
| Arg | Ala | Trp | Phe | Leu | His | Ile | His | Asn | Leu | Thr | Gly | Asn | Thr | Arg | Thr | |
| | | 180 | | | | | 185 | | | | | 190 | | | | |

| | | | | | |
|---|---|---|---|---|---|
| TAGCCCCAAA | CGCACCTCCC | ACCCTTGTCC | TATTTATCTA | TTTATTCAAC | TATTTATACA | 693 |
| AACGCCTATT | TATTCTTCTA | TTTATTCTTC | TATTTATTCA | GACAAAATAA | AGCTCTCCTT | 753 |
| TTCAACACTG | AAAA | | | | | 767 |

( 2 ) INFORMATION FOR SEQ ID NO:2:

( i ) SEQUENCE CHARACTERISTICS:
        ( A ) LENGTH: 162 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Cys | Asn | His | Leu | Arg | Pro | Gln | Asp | Ala | Thr | Phe | Ser | His | Asp | Ser | Leu |
| 1 | | | | 5 | | | | | 10 | | | | | 15 | |
| Gln | Leu | Leu | Arg | Asp | Met | Ala | Pro | Thr | Leu | Pro | Gln | Leu | Cys | Pro | Gln |
| | | | 20 | | | | | 25 | | | | | 30 | | |
| His | Asn | Ala | Ser | Cys | Ser | Phe | Asn | Asp | Thr | Ile | Leu | Asp | Thr | Ser | Asn |
| | | | 35 | | | | 40 | | | | | 45 | | | |
| Thr | Arg | Gln | Ala | Asp | Lys | Thr | Thr | His | Asp | Ile | Leu | Gln | His | Leu | Phe |
| | 50 | | | | | 55 | | | | | 60 | | | | |
| Lys | Ile | Leu | Ser | Ser | Pro | Ser | Thr | Pro | Ala | His | Trp | Asn | Asp | Ser | Gln |
| 65 | | | | | 70 | | | | | 75 | | | | | 80 |
| Arg | Gln | Ser | Leu | Leu | Asn | Arg | Ile | His | Arg | Tyr | Thr | Gln | His | Leu | Glu |
| | | | | 85 | | | | | 90 | | | | | 95 | |
| Gln | Cys | Leu | Asp | Ser | Ser | Asp | Thr | Arg | Ser | Arg | Thr | Arg | Trp | Pro | Arg |
| | | | 100 | | | | | 105 | | | | | 110 | | |
| Asn | Leu | His | Leu | Thr | Ile | Lys | Lys | His | Phe | Ser | Cys | Leu | His | Thr | Phe |
| | | 115 | | | | | 120 | | | | | 125 | | | |
| Leu | Gln | Asp | Asn | Asp | Tyr | Ser | Ala | Cys | Ala | Trp | Glu | His | Val | Arg | Leu |
| | 130 | | | | | 135 | | | | | 140 | | | | |
| Gln | Ala | Arg | Ala | Trp | Phe | Leu | His | Ile | His | Asn | Leu | Thr | Gly | Asn | Thr |
| 145 | | | | | 150 | | | | | 155 | | | | | 160 |
| Arg | Thr | | | | | | | | | | | | | | |

( 2 ) INFORMATION FOR SEQ ID NO:3:

( i ) SEQUENCE CHARACTERISTICS:
        ( A ) LENGTH: 269 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

| | | | | | |
|---|---|---|---|---|---|
| TTGGCCATCT | ATGAGATGCT | CCAGCAGATT | TTCAAAATCC | TCAGCAGCCC | CAGCACTCCA | 60 |
| GCCCACTGGA | ACGACAGACG | CGAACGCCAA | AGCCTCCTCA | CACCGGAGTC | CACCGCTACA | 120 |
| CCAGACCTGA | GCAATGCTTG | GACAGCAGAG | ACACGCTCTC | CGGACGCGAT | GGCCTCGCAA | 180 |

-continued

```
CCTTCACCTC  ACCATCAAAA  AACACTTCAG  CTGCCTCCAC  ACCTTCCTCC  AAGACAACGA          240

TTACACGCCT  GCGCTTGGAC  AGTGGTCCG                                               269
```

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
TTGGCCATCT  ATGAGATGCT  CCAGMANATH  TT                                           32
```

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGGACCACTG  TCCANGCRCA                                                           20
```